United States Patent [19]
Grunwald

[11] 4,303,293
[45] Dec. 1, 1981

[54] CONNECTION FOR ELECTRODES

[75] Inventor: Davor Grunwald, Winnipeg, Canada

[73] Assignee: Harco Electronics Limited, Winnipeg, Canada

[21] Appl. No.: 119,676

[22] Filed: Feb. 8, 1980

[30] Foreign Application Priority Data

Oct. 17, 1979 [CA] Canada .................................. 337819

[51] Int. Cl.³ ........................................... H01R 4/48
[52] U.S. Cl. .............................. 339/61 M; 339/75 M; 339/238
[58] Field of Search ................ 339/61 R, 75 R, 75 M, 339/74 R, 238, 239, 256 S, 273 R, 273 S, 274; 24/73 SA, 73 AP, 73 PB; 128/419 PS, 802, 803, 641, 644, 303.13

[56] References Cited

U.S. PATENT DOCUMENTS

| | | | |
|---|---|---|---|
| 3,829,826 | 8/1974 | Brown et al. | 128/641 X |
| 3,895,635 | 7/1975 | Justus et al. | 128/303.13 |
| 4,026,278 | 5/1977 | Ricketts et al. | 128/644 |
| 4,157,856 | 6/1979 | Schevchuk | 339/75 R |
| 4,178,052 | 12/1979 | Eekbom et al. | 339/261 X |
| 4,200,348 | 4/1980 | Stupay | 339/261 X |

*Primary Examiner*—Eugene F. Desmond

*Attorney, Agent, or Firm*—Birch, Stewart, Kolasch & Birch

[57] ABSTRACT

A connector for electrodes in the form of an electrode clip is provided herein which is formed of resilient plastic material, e.g., polypropylene. It includes a fixed jaw and a movable jaw, the jaws being provided with cooperating female electrical contacts. An operating mechanism is provided which is composed of a plurality of elements interconnected together by at least two living hinges, one of which being secured to the movable such jaw, and the other interconnecting two operating members but preferably having at least three living hinges, one of the living hinges being integrally secured to the movable such jaw, with the other two living hinges interconnecting three operating members. The operating mechanism includes an operating lever which is movable to urge one jaw towards the other jaw, and thus to urge the jaws into a closed position. This action simultaneously forces a preselected one of the living hinges to an over-toggle position to lock the jaws in such closed position. This electrode clip can be easily manipulated with one hand to secure the connector to the electrode stud which is disposed, e.g., on a human body, to a lead cable, e.g., of an electrocardiograph, without any pressure being applied directly to the stud and hence transmitted to the human body.

33 Claims, 12 Drawing Figures

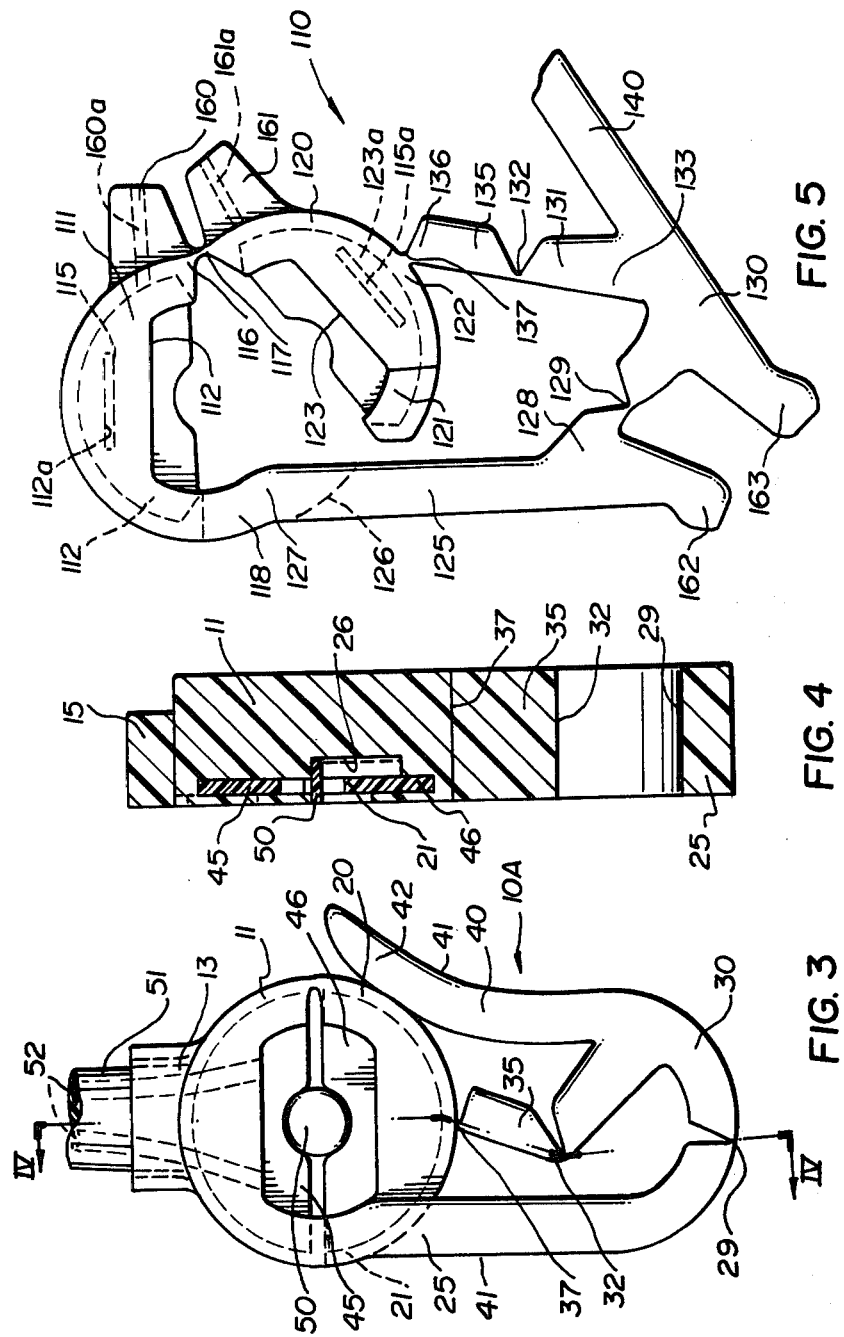

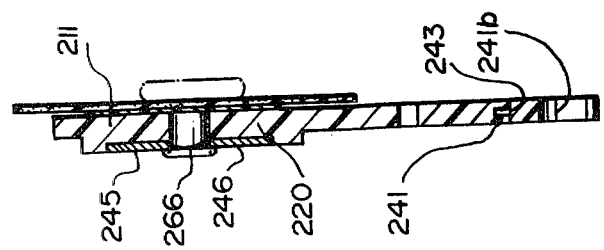
FIG. 11
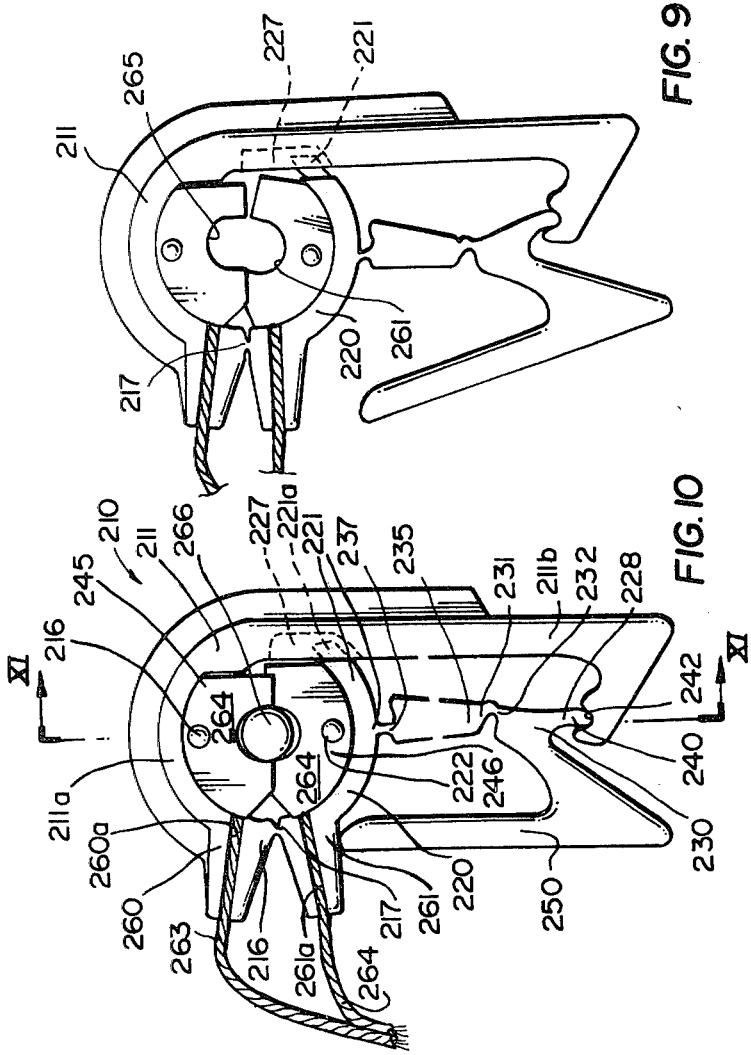
FIG. 9
FIG. 10

CONNECTION FOR ELECTRODES

BACKGROUND OF THE INVENTION (i) Field of the Invention

This invention relates to a connector for electrodes. More particularly, it relates to an electrode clip for the connection of a lead cable to an electrode which is secured to a human body.

(ii) Description of the Prior Art

In order to ascertain electrical phenomena arising from physiological functioning, for example electrocardiographic data associated with the functioning of the heart, e.g. in patient monitoring uses, it is necessary to apply sensory devices (known as electrodes) to the skin. The electrodes may be applied to the skin by a suction cup, aided by an electrically conductive cream, or they may be glued or taped to the patient's body. The electrode may be provided with a male pin or male snap fastener. Traditionally, the female portion of the snap fastener was intended mechanically to couple to the male portion. Several different types of cable fasteners have been used to couple electrical impulses from the electrode on a patient's body to a cable connected to an electrocardiograph or other monitoring device. It is important that a good connection be made by the electrode clip between the electrode and the lead cable.

Many deficiencies exist in such cable fasteners. For example, it was found that in many instances, the resulting electrical connection, however, was not noise-free and fatigued easily, causing loose connections. Additionally, since it was connected by pressing downward on the patient, a painfully hard push was often necessary to make a good connection. This type of snap fastener though simple and inexpensive to produce was difficult to repair.

One type of fastener which was developed to attempt to solve this problem was a hairpin and turn-cam fastener. This type of fastener made a good electrical connection when new and allowed simple application without pressing upon sensitive areas of the patient. The joint between cable and fastener was by a tubular solderless connector which was crimped on the fastener and the cable, and then covered with a shrink tubing. However, this fastener suffered many deficiencies. Unfortunately the fastener was expensive to make. It offered very little strain relief, and physically fatigued early in life, thereby causing loose connections. The electrical contact surface was only four pin point surfaces, which wore away very quickly. The length of the connector provided leverage which, when lifting the cable, often pried the connector off the snap. Because shielded wire cables work best when the exposed matellic fastenings were as small as possible, the length of this type of fastener was much too great to enhance the benefits of shielded cable. Also, whenever a patient rolled upon this type of fastener, he would likely receive a discomforting jab from its end, or cause the fastener to come off the electrode.

In an attempt to solve this problem, the cable fastener for electrocardiograph electrodes disclosed in U.S. Pat. No. 3,829,826 issued Aug. 13, 1974 to D. M. Brown et al was provided. In that cable fastener, there was included a metal bracket and a spring wire joined together. The metal bracket had a clearance hole which fit over the male snaps and had an offset to allow connections to cupmounted snaps. The spring wire provided mechanical retention, and by holding the bracket in contact with the snap, a durable electrical connection. A partial loop on the spring wire formed a finger pad for engaging and disengaging the fastener from the snap. The cable fastener mated with the male snap of an electrocardiograph electrode, for example, as it was mounted on a flat surface or seated in a cup depression. While this cable fastener was successful when new, as the spring became less resilient during use, it became less effective. On the other hand, if the spring were made strong initially, it would be more difficult to use.

In a second solution to this problem, that provided by U.S. Pat. No. 3,895,635 issued July 22, 1975 to G. F. Justus et al, a connector was provided which had a non-conductive body having one end of a cable located therein, carrying an electrical contact plate against which a stud of an electrode was locked by a non-conductive cam lever pivotally mounted on the body portion.

In a third solution, that provided by U.S. Pat. No. 4,026,278 issued May 31, 1977 to J. R. Ricketts et al, the electrode stud was inserted in a keyway hole in a connector secured electrically to the end of a cable, and held in place by a sprung back-up plate.

These latter two solutions, however, suffer the practical deficiency that in securing the connector to the electrode stud some pressure would be applied to the electrode, and thus to the human body. In many instances, this pressure against the human body is undesirable.

SUMMARY OF THE INVENTION (i) Aims of the Invention

Accordingly, it is among the objects of this invention to provide an electrode clip having the following features:
  (a) to be easily attached to the electrode terminal male snap without force being transmitted to the electrode;
  (b) to be electrically effective and positive to the male snap of the electrode;
  (c) not to be detachable without a definite action by the user;
  (d) to make positive contact to the electrode male snap through two separate contacts in the clip;
  (e) to "lock on" to the electrode so that a user will definitely know when the clip is properly attached;
  (f) to connect the metal contacts to a two-conductor wire in such a manner that they do not make contact with one another except through both of them contacting the male snap of the electrode;
  (g) to provide a slight interference fit with the top bulbous portion of the male snap;
  (h) to make positive but gentle electrical contact with the male snap of the electrode;
  (i) to be mechanically robust for substantial continued use and yet to provide adequate strain relief for the attached wire or wires;
  (j) to stay locked with movement of sheets or minor pressure as from a surgeon's arm pressing against the clip;
  (k) to be able to be used in a simple fashion by one hand operation.

(ii) Statement of Invention

Accordingly, this invention provides an electrode clip which is formed of resilient plastic material comprising: a fixed jaw, and a movable jaw pivotally urgeable towards the fixed jaw, the jaws including a pair of cooperating female electrical contacts; an operating mechanism composed of a plurality of interconnected elements and including at least two living hinges, one of the elements being integrally secured to the movable jaw by a living hinge; and a lever secured to the operating mechanism for operating on the operating mechanism for positively urging the movable jaw towards the fixed jaw; thereby to urge the jaws to a closed position and simultaneously to force one living hinge to an over-toggle position, and thus to lock the jaws in the closed position.

This invention also provides an electrode clip which is formed of a resilient plastic material comprising: a fixed jaw and a movable jaw pivotally secured at one end to one end of the fixed jaw by a living hinge and urgeable towards the fixed jaw, the jaws including a pair of cooperating female electrical contacts; an operating mechanism composed of a plurality of interconnected elements and including four living hinges, one terminal such living hinge being integral with the movable jaw, and another end of such living hinge being integral with an integral extension of the fixed jaw; the intermediate living hinges being interconnected to one another and a lever integral with the operating mechanism for operating on the operating mechanism for positively urging the movable jaw towards the fixed jaw; thereby to urge the jaws to a closed position and simultaneously to force one such living hinge to an over-toggle position, and thus to lock the jaws in the closed position.

This invention further provides an electrode clip which is formed of a resilient plastic material comprising: a fixed jaw and a movable jaw, pivotally secured at one end to one end of the fixed jaw by a living hinge, the jaws including a pair of cooperating female electrical contacts and electrical lead wire guiding and securing bosses; an operating mechanism composed of a plurality of interconnected elements and including four operating mechanism living hinges, one end of such living hinge being integral with the movable jaw, and another terminal end of such living hinge being integral with an extension of the fixed jaw; the intermediate living hinges being interconnected to one another a lever integral with the operating mechanism for operating the operating mechanism for positively urging the movable jaw towards the fixed jaw, whereby, upon operation of the lever action is effected to urge the jaws to a closed position and simultaneously to force one operating mechanism living hinge to an over-toggle position, and thus to lock the jaws in the closed position; and a release mechanism, integral with the extension of the fixed jaw and the operating mechanism for positively drawing the movable jaw away from the fixed jaw.

This invention provides, still further, an electrode clip which is formed of resilient plastic material comprising: a generally inverted J-shaped fixed jaw and a generally C-shaped movable jaw pivotally secured at one end to one end of the fixed jaw by a living hinge, the jaws including a pair of cooperating female electrical contacts and electrical lead wire guiding and securing bosses; an operating mechanism composed of a pair of elements interconnected by a living hinge, and having a fixed end and a free end the free end of one such element being integrally secured to the movable jaw by a living hinge, the free end of the other element being pivotally mounted at the free end of the fixed jaw; and a lever integral with the operating mechanism for operating on the operating mechanism for positively urging the movable jaw towards the fixed jaw; thereby to urge the jaws to a closed position and simultaneously to force one such living hinge of the operating mechanism to an over-toggle position, and thus to lock the jaws in the closed position.

This invention provides, still further, an electrode clip comprising: a fixed jaw, and a movable jaw pivotally urgeable towards the fixed jaw, the jaws including a pair of cooperating female electrical contacts; an operating mechanism composed of a plurality of interconnected elements and including at least two living hinges, one of the elements being integrally secured to the movable jaw by a living hinge; and a lever secured to the operating mechanism for operating on the operating mechanism for positively urging the movable jaw towards the fixed jaw, the lever including a spring section engaging the movable jaw section, whereby latching action is enhanced.

This invention also provides a blank, which is formed of resilient plastic material for distortion and assembly to provide an electrode clip, the blank including a first section adapted to provide an electrode engaging portion, and a second section adapted to provide an operating mechanism, (A) the first section comprising (a) a fixed semi-circular segment including a free end and a well within which is adapted to be secured a first female electrical contact, the fixed semi-circular segment including a rabbet therein; and (b) a movable semi-circular segment having a connected end and a free end, the segment being hingedly connected at the connected end to the free end of the fixed semi-circular segment by a living hinge, and having its free other end provided as a rabbet movable towards the fixed semi-circular element for slidable engagement within the rabbet, the movable element including a well within which is adapted to be secured a cooperating female electrical contact; and (B) the second section comprising (a) a first leg portion integrally joined at one end to the one free end of the fixed semi-circular segment; and adapted to provide an elongated element for the operating mechanism; (b) a second leg portion joined to the free end of the first leg portion by a living hinge, and adapted to provide an intermediate element of the operating mechanism; (c) a third leg portion joined to the free end of the second leg portion by a living hinge and to the movable semi-circular element by a living hinge, and adapted to provide a swingable element of the operating mechanism; and (d) an elongated extension of the second leg portion, and adapted to provide a lever for the operating mechanism.

OTHER FEATURES OF THE INVENTION

By one feature, the operating mechanism includes an elongated element integral with such fixed jaw.

By another feature, the operating mechanism includes an intermediate element connected to an elongated element which is integral with the fixed jaw, the intermediate element having the operating lever integrally secured thereto.

By yet another feature, one end of one such movable jaw is provided as a rabbet which slides in an associated rabbet in the fixed jaw.

By a further feature, one end of such movable jaw includes an abutment to limit its movement towards the fixed jaw.

By a further feature, the female electrode contacts include an indentation embracingly to engage an associated male electrode element.

By another feature, the electrode clip includes positively securing the female electrode contacts with the jaws.

By a further feature, the electrode clip includes means facilitating the electrical connection of lead electrode wires to one electrical contact.

By a variation thereof, the electrode clip includes a hollow boss on the fixed jaw, and a pair of channels passing longitudinally through the hollow boss to the fixed jaw, in order to facilitate the electrical connection of lead electrode wires to the electrical contact.

By another feature, the electrode contacts are located partially within slits in associated such jaws.

By a further feature, the electrode contacts are located partially within slits in associated such jaws and the female electrode contacts include an indentation embracingly to engage an associated male electrode element.

By yet another feature, the electrode contacts are located partially within slits in associated such jaws and including wedge means passing transversely through the jaws and associated electrode contacts for positively securing the female electrode contacts within the jaws.

By another feature, the lever is secured to the remaining elements of the operating mechanism by means of a ball and socket joint.

By another feature, the operating mechanism is secured to the lever by a fulcrum joint.

By yet another feature, the clip includes a projection in the lever and facing the spring section to ensure snap action.

By a variation thereof, the lever is pivotally secured to a semi-cylindrical fulcrum on the fixed jaw.

By another variation thereof, the fulcrum includes a guideway thereon.

By another feature, one end of the movable jaw includes a tenon which slides in a mortise in the fixed jaw.

By a further feature, the female electrodes are adapted to overlap one another, and including insulating material on the overlapping portions.

By yet another feature, the clip includes electrode wires secured to the female electrodes and held within the guiding and securing bosses.

By variations of all the aforesaid features, the electrode clip is formed of polypropylene.

By one feature of the blank of this invention, the blank includes a hollow boss integrally formed on the fixed semi-circular element.

By another feature, the blank includes gripping ribs formed on the first leg portion and on the elongated extension.

By yet another feature, the blank includes an arm-like extension formed in each of the first leg portion and the second leg portion.

By a further feature, the blank includes an ear on each of the fixed semi-circular element and the movable semi-circular element, adjacent the living hinge.

By another feature, the blank is injection molded from polypropylene, and consequently the electrode clip is formed from polypropylene.

BRIEF DESCRIPTION OF THE DRAWINGS

In the accompanying drawings,

FIG. 3 is a top plan view of the electrode clip of FIG. 2, in its "closed" position;

FIG. 4 is a cross section, along the line IV—IV of FIG. 3;

FIG. 5 is a top plan view of a second variant of the resilient plastic blank adapted to provide the electrode clip of this invention in its "as formed" condition;

FIG. 9 is a top plan view of the electrode clip of this invention in its assembled, but "open" position;

FIG. 10 is a top plan view of the electrode clip of FIG. 9 in its closed position engaging a male snap electrode;

FIG. 11 is a cross section along the line XI—XI of FIG. 10;

and

Figure 12:
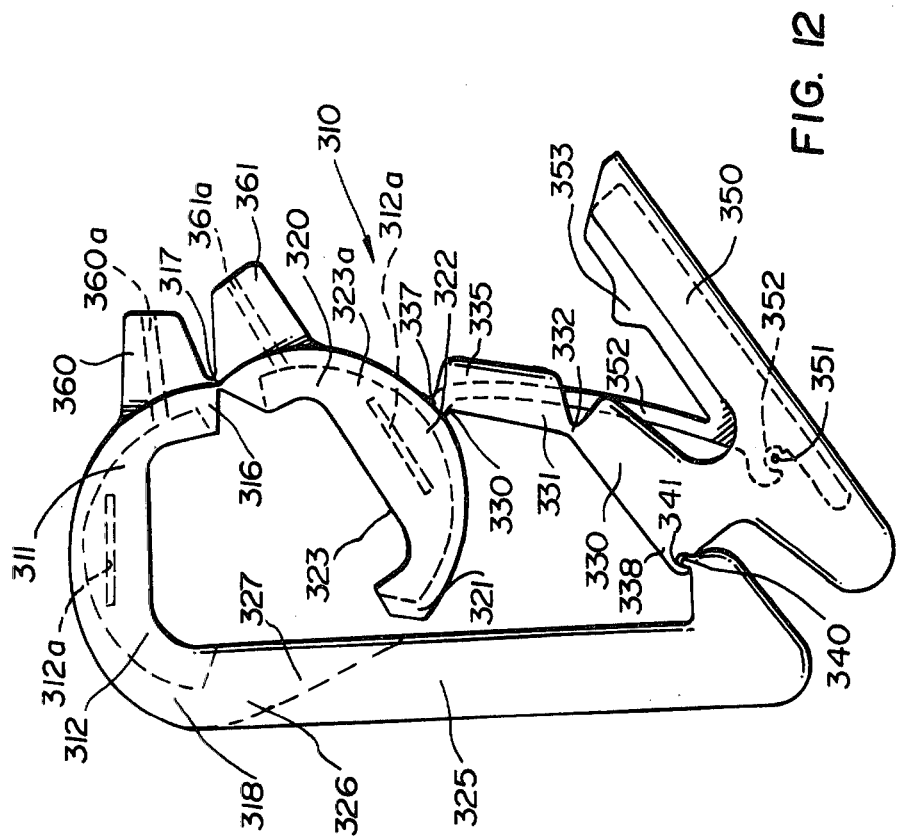

FIG. 12 is a side elevational view of the electrode clip of still another aspect of this invention in its unassembled "open" position.

DESCRIPTION OF PREFERRED EMBODIMENTS (i) Description of FIGS. 1-4

Figures 1, 2:
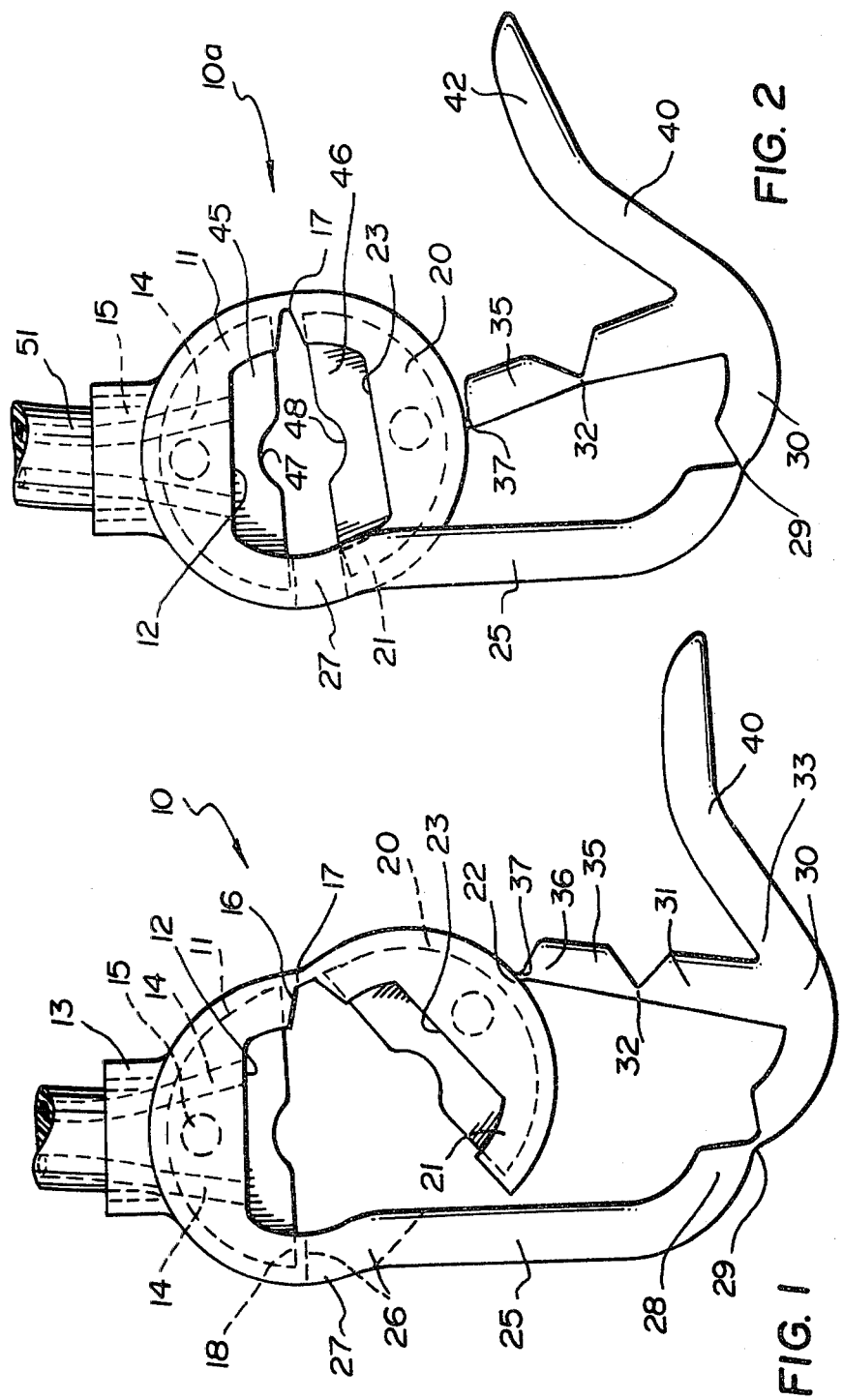
FIG. 1 is a top plan view of the resilient plastic blank adapted to provide the electrode clip of this invention in its "as formed" condition.
FIG. 2 is a top plan view of the electrode clip of this invention assembled from the resilient plastic blank of FIG. 1, in its "open" position.
Figure 8:
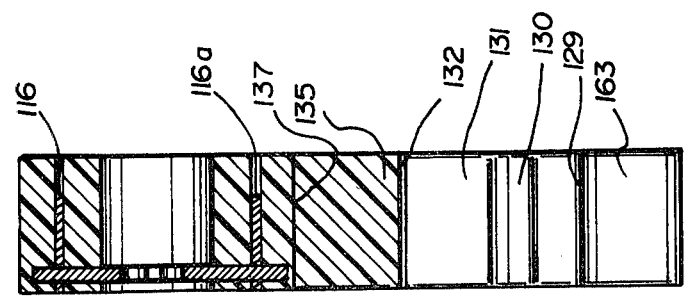
FIG. 8 is a cross section, along the line VIII—VIII of FIG. 7.

As seen in FIG. 1, the resilient plastic blank 10, preferably of injection molded polypropylene, includes a fixed semi-circular segment 11, which includes a well 12, and is surmounted by a boss 13. A pair of longitudinally extending channels 14 communicate from the interior of the hollow boss 13 to the well 12 for a purpose to be described hereinafter. A transverse bore 15 through segment 11 is also provided.

A movable segment 20 is secured to one end 16 of fixed segment 11 by means of a fulcrum "living hinge" 17, provided by a flexible web of the resilient plastic material. The preferred material for use in fabricating the electrode clip is polypropylene, primarily because of its performance at the flexible webs (or living hinges) where it has proved capable of withstanding repeated flexings without rupture or deterioration. Since, however, other resilient plastic material could be used with equivalent performance, the invention should not be limited to the use of polypropylene only. Movable segment 20 is also provided with a well 23. The free end 21 of movable segment 20 is somewhat thinner than the remainder of the segment 20 to provide a rabbet 21 for a purpose to be described hereinafter.

Fixed segment 11 and movable segment 20 together are thus adapted to provide a pair of pivotal jaws which are movable towards and away from one another.

Integrally connected to the other end 18 of fixed segment 11 is a first leg 25 of an operating mechanism. The connected end 26 of first leg 25 is provided with a rabbet 27, to accommodate thin rabbet 21 of movable segment 20, and to permit rabbet 21 to slide therein.

The free end 28 of first leg 25 is connected to a second, curved leg 30 by a first living hinge 29. In turn, curved leg 30 is connected at its free end 31 to a third leg 35 at a second living hinge 32. Finally, third leg 35 is connected at its free end 36 to a mid-portion 22 of movable segment 20 by a third living hinge 37.

An elongated extension 40 is integrally connected to a middle area 33 of second leg 30.

As seen in FIG. 2, the blank of FIG. 1 has been assembled into an electrode clip 10A. The rabbet 21 of movable segment 20 has been engaged with rabbet 27 in such a manner that it is free to slide therein. Segments 11 and 20 provide a pair of jaws. A first portion of a female electrode contact 45 has been secured within well 12. Electrode contact 45 is provided with an indentation adapted embracingly to engage a male electrode element (not shown) 47. Electrode contact 45 is also adapted to be connected to a wire of a lead cable 51 passing through hollow boss 15 and spaced-apart channels 14.

The jaw provided by movable segment 20 has a cooperating portion of a female electrode contact 46 secured within well 23. Electrode contact 46 is also provided with an indentation 48 adapted embracingly to engage a male electrical element.

The electrode clip in its closed condition electrically contacting male electrode stud 50 is shown in FIG. 3. Here, a lead cable 51 including two wires 52 has been secured to electrode contact 45 via bores 14.

In the electrode clip 10A, the first leg 25 now provides the elongated element of the operating mechanism. The second, curved leg 30 provides the intermediate element of the operating mechanism. The third leg 35 provides the swingable element of the operating mechanism. Finally, the elongated extension 40 becomes the operating lever of the operating mechanism.

(ii) Operation of the Embodiments of FIGS. 1–4

The closure of the electrode clip around the male electrode stud 50 is achieved in the following manner: The electrode contacts 45, 46 are first placed around the male electrode stud 50. The elongated element 25 and operating lever 40 are then grasped between the thumb and forefinger, using the ribs 41 as enhanced gripping surfaces, and the end 42 of the lever 40 is urged towards the movable jaw 20 by a clockwise rotation about living hinge 29. This causes the movable jaw 20 to rotate in a counterclockwise direction about living hinge 17 and urges rabbet 21 to slide generally upwardly in rabbet 27 and bring surfaces 47, 48 into close contact with male electrode stud 50. At the same time, swingable element 35 rotates in a clockwise direction with respect to movable jaw 20 about living hinge 37. Intermediate element 30 rotates in a counterclockwise direction with respect to swingable element 35 about living hinge 32. Eventually, when end 42 of operating lever 40 contacts movable jaw 20, living hinge 32 passes through its positive over-toggle position, and thus locks movable jaw 20 and electrode contact 46 against male electrode stud 50 and electrode contact 45.

Release is achieved simply by urging end 42 away from movable jaw 20, which urges living hinge 32 through its negative over-toggle position, to disconnect the electrical contacts between electrode contacts 45, 46 and male electrode stud 50.

(iii) Description of FIGS. 5–8

The embodiment of the invention shown in FIGS. 5–8 differs slightly from that shown in FIGS. 1–4. To the extent that similar parts are provided, they will be identified by a number 100 greater in amount than that of its similar part. Thus, as seen in FIG. 5, the resilient plastic blank 110, preferably of injection molded polypropylene, includes a fixed semi-circular segment 111, which includes a well 112 and a fixing slot 112a. Integral with segment 111 is an electrode lead wire guiding and securing boss 160 having a channel 160a therein of less thickness than segment 111. A transverse slot 115 through segment 111 is also provided.

A movable segment 120 is secured to one end 116 of fixed segment 111 by means of a fulcrum "living hinge" 117, provided by a flexible web of the resilient plastic material. Movable segment 120 is also provided with a well 123 and a fixing slot 123a. An integral electrode lead wire guiding and securing boss 161 having channel 161a therein of less thickness than segment 120 is provided adjacent living hinge 117. The free end 121 of movable segment 120 is somewhat thinner than the remainder of the segment 120 to provide a rabbet 121 for a purpose to be described hereinafter.

Fixed segment 111 and movable segment 120 together are thus adapted to provide a pair of pivotal jaws movable towards and away from each other.

Integrally connected to the other end 118 of fixed segment 111 is a first leg 125 of an operating mechanism. The connected end 126 of first leg 125 is provided with a rabbet 127, to accommodate thin rabbet 121 of movable segment 120, and to permit rabbet 121 to slide therein.

The free end 128 of first leg 125 is connected to a second, curved leg 130 by a first living hinge 129. In turn, curved leg 130 is connected at its free end 131 to a third leg 135 at a second living hinge 132. Finally, third leg 135 is connected at its free end 136 to a mid-portion 122 of movable segment 120 by a third living hinge 137.

An elongated extension 140 is integrally connected to a middle area 133 of second leg 130.

A pair of arms 162 integral with first leg 125 and 163 integral with second leg 139 are also formed for a purpose to be described hereinafter.

Figure 7:
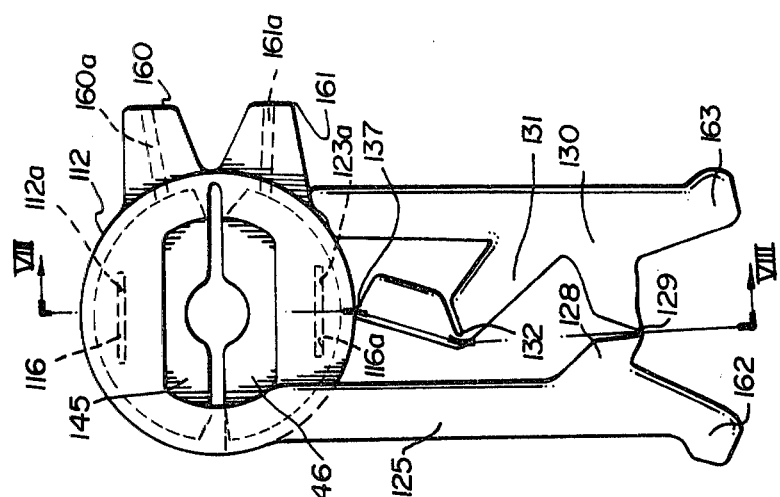
FIG. 7 is a top plan view of the electrode clip of FIG. 6, in its "closed" position.
Figure 6:
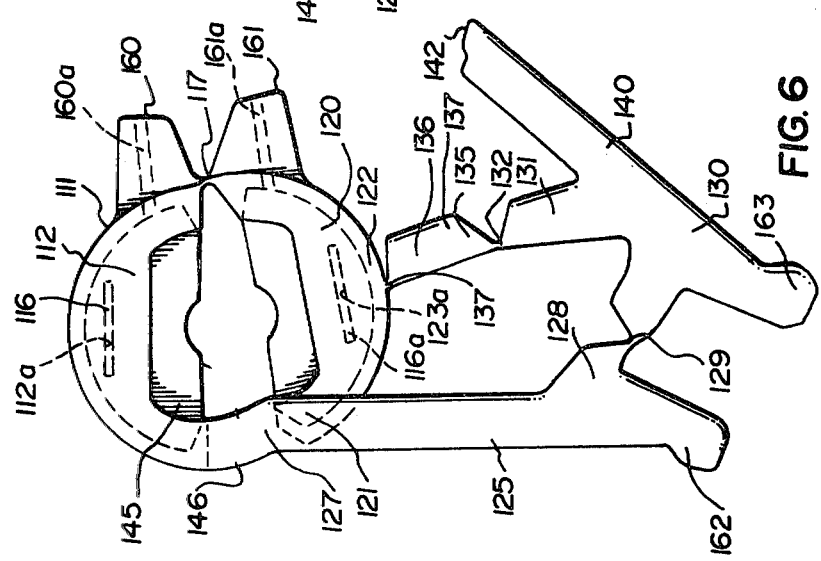
FIG. 6 is a top plan view of the electrode clip of this invention, assembled from the resilient plastic blank of FIG. 5, in its "open" position.

FIGS. 6 and 7 show the electrode clip 110 as including fixed segment 111 connected to movable segment 120 via living hinge 117, to provide a pair of movable jaws, with rabbet 121 of movable segment 120 being slidably engaged within rabbet 127. Electrode contact 145 is secured in well 112 via fixing slot 112a and electrode contact 146 is similarly secured within well 123 via fixing slot 123a. In addition, wedge element 116 secures electrode contact 145 within slot 112a and wedge element 116a secures electrode contact 146 within slot 123a.

Bosses 160 on fixed jaw 111 and 161 on movable jaw 120 enable electrode lead wires to be secured to electrode contacts 145, 146.

Operating mechanism includes the elongated element provided by the first leg 125, connected to intermediate element provided by the second leg 130 via a living hinge 129. The intermediate element 130 is connected to swingable element provided by third leg 135 via a living hinge 132. The swingable element 135 is connected to movable jaw 120 via living hinge 137.

(iv) Operation of the Embodiment of FIGS. 5–8

The pair of arm-like extensions 162 enable more positive disengagement and disconnecting of the electrode clip. Thus, the closing of the clip is performed in the same manner as that described for the first embodiment. However, to disconnect the electrode clip, it is merely necessary to grasp arms 162, 163 between the thumb and forefinger and draw them closer together. This positively moves living hinge 132 to its negative over-toggle position, thus releasing the electrical connection.

(v) Description of FIGS. 9-11

The embodiment of FIGS. 9-11 differs from those shown previously in FIGS. 1-8. However, to the extent that similar parts are provided, they will be identified by a number 200 greater in amount than that of a similar part in FIGS. 1-4. Thus, as seen in FIGS. 9 and 10, the resilient plastic electrode clip 210, preferably of injection molded polypropylene, includes a generally J-shaped fixed jaw 211 including a semi-circular segment 211a and an elongated tail 211b. Semi-circular segment 111a includes means for securing an electrode contact plate therein. An electrode lead wire guiding and securing boss 260 having a channel 260a therein of less thickness than segment 211 is provided adjacent one end of semi-circular segment 211a. The wall of elongated tail 211b adjacent semi-circular segment 211a is provided with mortise 227.

Movable segment 220 is secured to one free end 216 of semi-circular segment 211a by means of a fulcrum "living hinge" 217, provided by a flexible web of the resilient plastic material. Movable segment 220 is also provided with means for securing an electrode contact plate therein. A second electrode lead wire guiding and securing boss 261 having a channel 261a therein of less thickness than segment 220 is provided adjacent living hinge 217. The free end 221 of movable segment 220 is provided as a mortise 221a for a purpose to be described hereinafter.

Semi-circular fixed segment 211a and movable segment 220 together are thus adapted to provide a pair of pivotal jaws, movable towards and away from each other.

The operating mechanism includes a first leg 235 connected integrally at its free end 236 to a mid-portion 222 of movable segment 220 by a first living hinge 237. First leg 235 is connected integrally at its free end 231 to the free end of a second leg 230 at a second living hinge 232. The free end 228 of second leg 230 is provided as a cylindrical fulcrum rod 240 including a central guiding slot 241 therein. This cylindrical rod is adapted to be pivotal around semi-cylindrical bushing 242 provided with a central guiding wall 243 thereon.

Actuating lever 250, integrally secured to second leg 230, is provided for urging the jaws to a closed position.

FIGS. 9 and 10 show electrode clip 210 as including J-shaped fixed jaw 211 connected to movable segment 220 via living hinge 217, to provide a pair of movable jaws, with tenon end 221a of movable segment 220 being slidably engaged within mortise 227. Electrode contact plate 245 is secured to fixed jaw 211 by means of rivet 216, and is secured to electrode lead wire 263, as by soldering. Similarly, electrode contact plate 246 is secured in well 223 by rivet 222 and is secured to electrode lead wire 264, as by soldering. The electrode plates are provided with semi-circular cut-outs 265 so that the electrode plates can grip male contact pin 266. The overlapping portions of electrodes 245, 246 are provided with electrical insulation, e.g., a plastic coating. It will be seen, moreover, that bosses 260, 261 enable the electrode wires 263, 264 to be secured to electrode contacts 245, 246.

(vi) Operation of the Embodiment of FIGS. 9-11

The closing of the electrode clip of this embodiment of this invention is performed in the same manner as that described for the previous two embodiments.

(vii) Description of FIG. 12

The embodiment of FIG. 12 shows an alternative embodiment using only two living hinges, a ball and socket hinge, and a spring member. The spring member provides spring action and over-center function. As shown, the electrical connections and the electrodes have been omitted for clarity, but they are the same as shown in FIGS. 5-8. To the extent that the embodiment of FIG. 12 is similar to the embodiment of FIGS. 5-8, the same basic reference numerals will be used, but increased by 200, to appear as a "300" series. Thus, as seen in FIG. 12, the resilient plastic blank 310, preferably of injection molded polypropylene, includes a fixed semi-circular segment 311, which includes a well 312 and a fixing slot 312a. Integral with segment 311 is an electrode lead wire guiding and securing boss 360 having channel 360a therein of less thickness than segment 311. A transverse slot 115 through segment 311 is also provided.

A movable segment 320 is secured to one end 316 of fixed segment 311 by means of a fulcrum "living hinge" 317, provided by a flexible web of the resilient plastic material. Movable segment 320 is also provided with a well 323 and a fixing slot 323a. Integral with segment 320 is an electrode lead wire guiding and securing boss 361 having channel 361a therein of less thickness than segment 320 provided adjacent living hinge 317. The free end 321 of movable segment 320 is somewhat thinner than the remainder of the segment 320 to provide a rabbet 321 for a purpose to be described hereinafter.

Fixed segment 311 and movable segment 320 together are thus adapted to provide a pair of pivotal jaws movable towards and away from each other.

Integrally connected to the other end 318 of fixed segment 311 is a main leg 325 of an operating mechanism. The connected end 326 of main leg 325 is provided with a rabbet 327 to accommodate thin rabbet 321 of movable segment 320, and to permit 321 to slide therein.

The operating mechanism includes a first leg 335 connected integrally at its free end 336 to a mid-portion 322 of movable segment 320 by a first living hinge 337. First leg 335 is connected integrally at its free end 311 to the free end of a second leg 330 at a second living hinge 332. The free end 328 of second leg 330 is provided with a central guiding slot 341 to cooperate with a cylindrical fulcrum rod 340. This cylindrical rod 340 is adapted to be pivotal around semi-cylindrical bushing 342 provided with a central guiding wall 343 thereon.

Actuating lever 350 is secured to second leg 330 by a ball 351 on second leg 330 and a socket 351 on activating lever 350. The activating lever 350 includes a spring section 352 which is connected to the movable jaw section 320 and a facing projection 353 to ensure a snap action. This ball and socket type hinge snaps together.

(viii) Operation of the Embodiment of FIG. 12

The closing of the electrode clip of this embodiment of this invention is performed in the same manner as that described for the previous two embodiments. However, the spring section puts the living hinges more in compression and enhances the latching action.

SUMMARY

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What I claim is:

1. An electrode clip formed of resilient plastic material comprising:
   a fixed jaw, and a movable jaw pivotally urgeable towards the fixed jaw, said jaws including a pair of cooperating female electrical contacts;
   an operating mechanism composed of a plurality of interconnected elements and including at least two living hinges, one of the elements being integrally secured to said movable jaw by a living hinge;
   and a lever secured to said operating mechanism for operating on said operating mechanism for positively urging said movable jaw towards said fixed jaw;
   thereby to urge said jaws to a closed position and simultaneously to force one said living hinge to an over-toggle position, and thus to lock said jaws in said closed position.

2. An electrode clip formed of resilient plastic material comprising:
   a fixed jaw and a movable jaw pivotally secured at one end to one end of said fixed jaw by a living hinge and urgeable towards the fixed jaw, said jaws including a pair of cooperating female electrical contacts;
   an operating mechanism composed of a plurality of interconnected elements and including four living hinges, one said living hinge being integral with said movable jaw, and another said living hinge being integral with an integral extension of said fixed jaw the intermediate living hinges being interconnected to one another;
   and a lever integral with said operating mechanism for operating on said operating mechanism for positively urging said movable jaw towards said fixed jaw;
   thereby to urge said jaws to a closed position and simultaneously to force one said living hinge to an over-toggle position, and thus to lock said jaws in said closed position.

3. An electrode clip formed of resilient plastic material comprising:
   a fixed jaw and a movable jaw, pivotally secured at one end to one end of said fixed jaw by a living hinge, said jaws including a pair of cooperating female electrical contacts and electrical lead wire guiding and securing bosses;
   an operating mechanism composed of a plurality of interconnected elements and including four operating mevchanism living hinges, one said living hinge being integral with said movable jaw, and another end of said living hinge being integral with an extension of said fixed jaw the intermediate living hinges being interconnected to one another;
   a lever integral with said operating mechanism for operating said operating mechanism for positively urging said movable jaw towards said fixed jaw, whereby, upon-operation of said lever action is effected to urge said jaws to a closed position and simultaneously to force one said operating mechanism living hinge to an over-toggle position, and thus to lock said jaws in said closed position;
   and a release mechanism, integral with said extension of said fixed jaw and said operating mechanism for positively drawing said movable jaw away from said fixed jaw.

4. An electrode clip formed of resilient plastic material comprising:
   a generally inverted J-shaped fixed jaw and a generally C-shaped movable jaw pivotally secured at one end to one end of said fixed jaw by a living hinge, said jaws including a pair of cooperating female electrodes and electrical lead wire guiding and securing bosses;
   an operating mechanism consisting essentially of a pair of elements interconnected by a living hinge, having a fixed end and a free end the free end of one said element being integrally secured to said movable jaw by a living hinge, the free end of said other element being pivotally mounted at the free end of said fixed jaw;
   and a lever integral with said operating mechanism for operating on said operating mechanism for positively urging said movable jaw towards said fixed jaw;
   thereby to urge said jaws to a closed position and simultaneously to force one said living hinge of said operating mechanism to an over-toggle position, and thus to lock said jaws in said closed position.

5. The electrode clip of claim 1 wherein said operating mechanism includes an elongated element integral with said fixed jaw.

6. The electrode clip of claim 1 wherein said operating mechanism includes an intermediate element connected to an elongated element which is integral with said fixed jaw, said intermediate element having said operating lever integrally secured thereto.

7. The electrode clip of claim 1 wherein one end of one said movable jaw is provided as a rabbet which slides in an associated rabbet in said fixed jaw.

8. The electrode clip of claim 1 wherein one end of said movable jaw includes an abutment to limit its movement toward said fixed jaw.

9. The electrode clip of claim 1 wherein said female electrode contacts include an indentation embracingly to engage an associated male electrode element.

10. The electrode clip of claim 1 including means positively securing said female electrode contacts within said jaws.

11. The electrode clip of claim 1 including means facilitating the electrical connection of lead electrode wires to one said electrical contact.

12. The electrode clip of claim 1 including a hollow boss on said fixed jaw, and a pair of channels passing longitudinally through said hollow boss to said fixed jaw, in order to facilitate the electrical connection of lead electrode wires to said electrical contact.

13. The electrode clip of claim 1 wherein said electrode contacts are located partially within slits in associated said jaws.

14. The electrode clip of claim 1 wherein said electrode contacts are located partially within slits in associated said jaws and wherein said female electrode contacts include an indentation embracingly to engage an associated male electrode element.

15. The electrode clip of claim 1 wherein said electrode contacts are located partially within slits in associated said jaws and including wedge means passing transversely through said jaws and associated electrode contacts for positively securing said female electrode contacts within said jaws.

16. The electrode clip of claim 4 wherein said lever is pivotally secured to a semi-cylindrical fulcrum on said fixed jaw by means of a cylindrical pivot.

17. The electrode clip of claim 16 wherein said fulcrum includes a guideway thereon.

18. The electrode clip of claim 4 wherein one end of said movable jaw includes a tenon which slides in a mortise in said fixed jaw.

19. The electrode clip of claim 4 wherein said female electrodes are adapted to overlap one another, and including insulating material on said overlapping portions.

20. The electrode clip of claim 4 wherein said female electrodes are provided with male electrode engaging indentations.

21. The electrode clip of claim 4 including electrode wires secured to said female electrodes and held within said guiding and securing bosses.

22. The electrode clip of claim 1 formed of polypropylene.

23. The electrode clip of claim 4 formed of polypropylene.

24. An electrode clip formed of resilient plastic material comprising:
a fixed jaw, and a movable jaw pivotally urgeable towards the fixed jaw, said jaws including a pair of cooperating female electrical contacts;
an operating mechanism composed of a plurality of interconnected elements and including at least two living hinges, one of the elements being integrally secured to said movable jaw by a living hinge;
and a lever secured to said operating mechanism for operating on said operating mechanism for positively urging said movable jaw towards said fixed jaw, said lever including a spring section engaging said movable jaw section, whereby latching action is enhanced.

25. The electrode clip of claim 24 wherein said lever is secured to the remaining elements of said operating mechanism by means of a ball and socket joint.

26. The electrode clip of claim 24 wherein the operating mechanism is secured to said lever by a fulcrum joint.

27. The electrode clip of claim 24 including a projection on said lever and facing said spring section to ensure snap action.

28. A blank formed of resilient plastic material for distortion and assembly to provide an electrode clip, said blank including a first section adapted to provide an electrode engaging portion, and a second section adapted to provide an operating mechanism,
(A) said first section comprising:
(a) a fixed semi-circular segment including a free end and a well within which is adapted to be secured a first female electrical contact, said fixed semi-circular segment including a rabbet therein,
and
(b) a movable semi-circular segment having a connected end and a free end, said segment being hingedly connected at said connected end to said free end of said fixed semi-circular segment by a living hinge, and having its free other end provided as a rabbet movable towards said fixed semi-circular element for slidable engagement within said rabbet, of said fixed segment said movable segment including a well within which is adapted to be secured a cooperating female electrical contact;
and
(B) said second section comprising
(a) a first leg portion integrally joined at one end to another end of said fixed semi-circular segment and adapted to provide an elongated element of said operating mechanism;
(b) a second leg portion joined to the free end of said first leg portion by a living hinge, and adapted to provide an intermediate element of said operating mechanism;
(c) a third leg portion joined to the free end of said second leg portion by a living hinge and to said movable semi-circular element by a living hinge, and adapted to provide a swingable element of said operating mechanism;
and
(d) an elongated extension of said second leg portion, and adapted to provide a lever for said operating mechanism.

29. The blank of claim 28 including an hollow boss integrally formed on said fixed semi-circular segment.

30. The blank of claim 28 including gripping ribs formed on said first leg portion and on said elongated extension.

31. The blank of claim 28 including an arm-like extension formed in each of said first leg portion and said second leg portion.

32. The blank of claim 28 including an ear on each of said fixed semi-circular segment and said movable semi-circular segment adjacent said living hinge.

33. The blank of claim 28 injection molded from polypropylene.

* * * * *